United States Patent [19]

Schmidt et al.

[11] Patent Number: 5,101,034

[45] Date of Patent: Mar. 31, 1992

[54] PREPARATION OF HETEROARYLOXYACETAMIDES

[75] Inventors: Thomas Schmidt, Haan; Hans-Joachim Diehr, Wuppertal, both of Fed. Rep. of Germany

[73] Assignee: Bayer Aktiengesellschaft, Leverkusen, Fed. Rep. of Germany

[21] Appl. No.: 668,796

[22] Filed: Mar. 7, 1991

Related U.S. Application Data

[63] Continuation of Ser. No. 538,599, Jun. 14, 1990, abandoned, which is a continuation of Ser. No. 741,098, Jun. 4, 1985, abandoned.

[30] Foreign Application Priority Data

Jun. 20, 1984 [DE] Fed. Rep. of Germany ....... 3422861

[51] Int. Cl.$^5$ .......................................... C07D 285/13
[52] U.S. Cl. ................................... 548/136; 540/603; 544/133; 544/134; 544/135; 544/137; 544/138; 544/367; 544/368; 544/369; 546/19; 546/164; 546/168; 546/198; 546/209; 548/129; 548/132; 548/144; 548/171; 548/187; 548/221; 548/229
[58] Field of Search ............... 548/129, 132, 136, 144, 548/187, 221, 229; 540/603; 544/133, 134, 135, 137, 138, 367, 368, 369; 546/19, 164, 168, 198, 209

[56] References Cited

U.S. PATENT DOCUMENTS

| 4,364,769 | 12/1982 | Pissiotas | 71/90 |
|---|---|---|---|
| 4,408,055 | 10/1983 | Forster | 548/125 |
| 4,455,428 | 6/1984 | Diehr et al. | 548/187 |
| 4,708,731 | 11/1987 | Forster | 548/136 |

FOREIGN PATENT DOCUMENTS

| 0005501 | 11/1979 | European Pat. Off. | 548/136 |
|---|---|---|---|
| 0018497 | 11/1980 | European Pat. Off. | 548/136 |
| 0044497 | 1/1982 | European Pat. Off. | 548/136 |
| 3038636 | 5/1982 | Fed. Rep. of Germany | 548/136 |

OTHER PUBLICATIONS

March, Ad. Org. Chem., 3rd ed., pp. 320–322, 548–586 (1985).

*Primary Examiner*—Robert Gerstl
*Attorney, Agent, or Firm*—Sprung Horn Kramer & Woods

[57] ABSTRACT

A process for the preparation of a heteroaryloxyacetamide of the formula

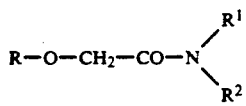

in which
R is a 5 membered heterocycle which may be benzofused, and
$R^1$ and $R^2$ each independently is hydrogen, alkyl, alkenyl, alkynyl, cycloalkyl or cycloalkenyl, halogenoalkyl, alkoxyalkyl, alkoxy, aralkyl or aryl, or
$R^1$ and $R^2$, together with the nitrogen atom to which they are bonded, form a heterocycle, which comprises reacting a sulphonylated heteroaromatic of the formula $$R-SO_2-R'$$

in which
R' is lower alkyl or benzyl,
with an α-oxyacetamide of the formula

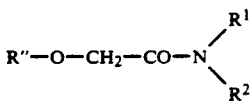

in which
R" is hydrogen or acyl,
in the presence of an inorganic base as an acid acceptor and of solvent as a diluent at a temperature of about −50° C. to +150° C. The products are known herbicides.

6 Claims, No Drawings

PREPARATION OF HETEROARYLOXYACETAMIDES

This application is a continuation of application Ser. No. 538,599, filed June 14, 1990, now abandoned which is a continuation of Ser. No. 741,098, filed June 4, 1985, now abandoned.

The invention relates to a new process for the preparation of known heteroaryloxyacetamides having a herbicidal activity.

It is already known that heteroaryloxyacetamides, for example the herbicidally active N-methyl(5-trifluoromethyl-1,3,4-thiadiazol-2-yl)oxyacetanilide, are obtained by reacting hydroxyacetamides, for example N-methylhydroxyacetanilide, with corresponding halogen-substituted heteroaromatics, for example 2-chloro-5-trifluoromethyl-1,3,4-thiadiazole, in the presence of an acid-binding agent, using an organic or aqueous diluent (cf. patent documents EP-A-0,005,501, EP-A-0,018,487, DE-OS 3,038,636 and DE-OS 3,148,839). A disadvantage of this process is the use of halogen-substituted heteroaromatics as starting materials, because they often cannot be prepared in relatively large quantities in a simple manner, in good yield and purity, and, if costly purification operations are omitted, the by-products and impurities present in the starting materials are also carried through into the end products.

It has now been found that the known herbicidally active heteroaryloxyacetamides of the general formula (I)

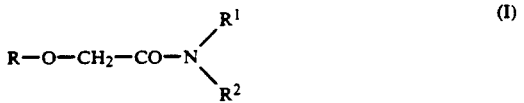

in which
- R represents an optionally substituted 5-membered heterocycle which can also be benzo-fused and
- $R^1$ and $R^2$ independently of one another represent hydrogen, alkyl, alkenyl, alkynyl, optionally substituted cycloalkyl or cycloalkenyl, halogenoalkyl, alkoxyalkyl, alkoxy, aralkyl and optionally substituted aryl or
- $R^1$ and $R^2$, together with the nitrogen atom to which they are bonded, represent an optionally substituted, saturated or unsaturated heterocycle which can contain further heteroatoms, are obtained in good yields and high purity by reacting sulphonylated heteroaromatics of the general formula (II)

$$R-SO_2-R'  \quad (II)$$

in which
- R has the meaning given above and
- R' represents lower alkyl or optionally substituted benzyl, with α-oxyacetamides of the general formula (III)

in which

R" represents hydrogen or acyl and
$R^1$ and $R^2$ have the meanings given above,
in the presence of an inorganic base as an acid acceptor and of an organic or inorganic solvent as a diluent, if appropriate in the presence of a phase transfer catalyst, at temperatures of $-50°$ C. to $+150°$ C.

It is to be regarded as extremely surprising that the reaction of sulphonylated heteroaromatics of the formula (II) with α-oxyacetamides of the formula (III), in the presence of simple inorganic bases such as aqueous sodium hydroxide or potassium carbonate, proceeds with good yields, since it is known from the state of the art that substitution reactions of this type only proceed with catalysis by strongly basic and hydrolysis-sensitive organic bases, for example alcoholates (cf. E. Hoggarth, J. Chem. Soc. 1949, 3311-3325). Moreover, it is surprising that, under the reaction conditions in the strongly basic reaction medium, the amide groups both the starting materials of the formula (III) and in the end products of the formula (I) are not saponified, but remain unmodified.

An advantage of the process according to the invention is that the sulphonylated heteroaromatics used as starting compounds can be prepared easily, in large quantities and in outstanding purity from the corresponding thioethers, which are also readily available, without the need for costly purification operations. Another advantage of the new process consists of the high yields of heteroaryloxyacetamides of the formula (I), which in many cases exceed the yield of the known processes.

The process according to the invention makes it possible preferably to obtain compounds of the formula (I) in which
- R represents a 5-membered heterocycle optionally substituted by one or more identical or different substituents, which can also be benzo-fused and which can contain, as heteroatoms, 1 to 3 nitrogen atoms and in addition an oxygen atom or a sulphur atom, the following being suitable substituents: halogen, cyano, nitro, straight-chain or branched alkyl, alkoxy or alkylthio each having up to 4 carbon atoms, straight-chain or branched halogenoalkyl having up to 4 carbon atoms and up to 9 identical or different halogen atoms, aralkyl, aralkoxy or aralkylthio each having 6 or 10 carbon atoms in the aryl moiety and 1 to 2 carbon atoms in the alkyl moiety, as well as aryl having 6 or 10 carbon atoms, which is optionally substituted by one to three identical or different substituents chosen from $C_{1-4}$-alkyl, $C_{1-4}$-alkoxy, halogen or $C_{1-4}$-halogenoalkyl, and
- $R^1$ and $R^2$ independently of one another represent hydrogen, straight-chain or branched alkyl having 1 to 8 carbon atoms, straight-chain or branched alkenyl and alkynyl each having 2 to 8 carbon atoms, cycloalkyl or cycloalkenyl each having 3 to 7 carbon atoms, which are optionally substituted by one or more identical or different substituents (suitable substituents being, in particular, alkyl radicals having 1 to 4 carbon atoms), straight-chain or branched alkoxy and alkoxyalkyl having 1 to 8 carbon atoms, halogenoalkyl having 1 to 8 carbon atoms and 1 to 5 halogen atoms (in particular fluorine, chlorine and bromine), aralkyl having 6 to 10 carbon atoms in the aryl moiety and 1 to 2 carbon atoms in the alkyl moiety, as well as aryl having 6 or 10 carbon atoms, which is optionally substituted by one or more identical or different substituents, the following being suitable substituents: halogen, straight-chain or branched alkyl, alkoxy or alkylthio each having 1 to 4 carbon atoms, halogenoalkyl, halogenoalkoxy and halogenoalkylthio each having 1 to 2 carbon atoms and 1 to 5 halogen atoms, in particular fluorine, chlorine or bromine, as well as nitro, or $R^1$ and $R^2$, together with the nitrogen atom to which they are bonded, represent a saturated or unsaturated, 5-membered to 7-membered heterocycle optionally substituted by one or more identical or different substituents, which can contain up to 2 further heteroatoms, in particular nitrogen or oxygen, the following being suitable substituents: straight-chain or branched alkyl having 1 to 6 carbon atoms, also in the form of a fused ring system, aryl having 6 or 10 carbon atoms, also in the form of a fused ring system, or dioxyalkylene having 2 to 3 carbon atoms.

The process according to the invention relates particularly preferably to compounds of the formula (I) in which R represents one of the heterocycles

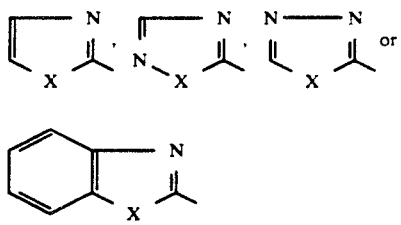

X representing oxygen or sulphur, which can optionally be substituted by one or more identical or different substituents, the following substituents being mentioned in particular: fluorine, chlorine, bromine, cyano, nitro, methyl, ethyl, n- and i-propyl, n-, i-, s- and t-butyl, methoxy, ethoxy, methylthio, trifluoromethyl, trichloromethyl, fluorodichloromethyl, difluorochloromethyl, benzyl, benzyloxy and benzylthio, as well as phenyl optionally substituted by one to three identical or different substituents chosen from methyl, methoxy, chlorine or trifluoromethyl, and $R^1$ and $R^2$ independently of one another represent hydrogen, straight-chain or branched alkyl having 1 to 6 carbon atoms, straight-chain or branched alkenyl and alkynyl each having 2 to 8 carbon atoms, cycloalkyl or cycloalkenyl having 5 to 7 carbon atoms, which are optionally substituted by one to three identical or different substituents chosen from methyl or ethyl, branched or straight-chain alkoxy and alkoxyalkyl having 1 to 6 carbon atoms, halogenoalkyl having 1 to 6 carbon atoms and 1 to 5 halogen atoms (in particular fluorine, bromine and chlorine), and benzyl, as well as phenyl optionally substituted by one to three identical or different substituents, the following substituents being particularly preferred: methyl, ethyl, methoxy, methylthio, trifluoromethyl, trifluoromethoxy, trifluoromethylthio, fluorine, chlorine and nitro, or $R^1$ and $R^2$, together with the nitrogen atom to which they are bonded, represent the heterocycles of the formulae:

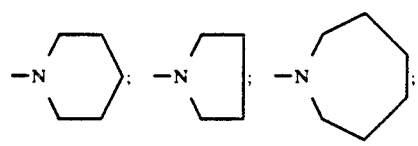

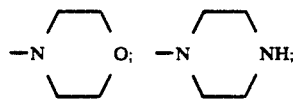

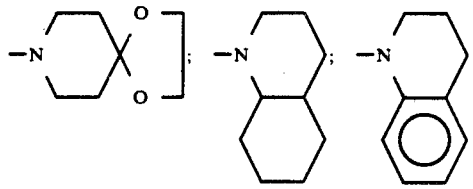

optionally substituted by one to three identical or different substituents, the following being particularly preferred substituents: methyl, ethyl and phenyl.

If, for example, N-methyl-hydroxyacetanilide and 2-methylsulphonyl-5-trifluoromethyl-1,3,4-thiadiazole are used as starting materials, the reaction course of the process according to the invention can be represented by the following equation:

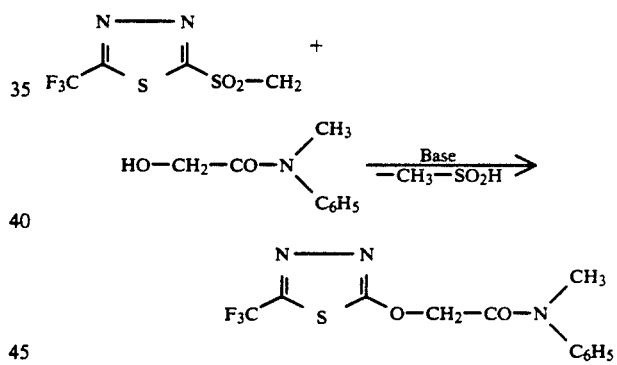

The sulphonylated heteroaromatics required as starting materials for the process according to the invention are generally defined by the formula (II). In this formula, R preferably represents those heterocyclic radicals which were mentioned as preferred in the description of the corresponding radicals of the compounds of the formula (I), and R' preferably represents methyl or ethyl.

The sulphonylated heteroaromatics of the formula (II) are known or can be obtained in a simple manner by known processes (cf., for example, J. Chem. Soc. 1949, pages 1918-1923; J. Chem. Soc. 1949, pages 3311-3315; also Chem. Abstr. Vol. 67, 89998k (1967); Chem. Abstr. Vol. 68, 2169q (1968); U.S. Pat. No. 2,562,284; German Offenlegungsschrift 2,533,604; German Offenlegungsschrift 2,533,605; German Offenlegungsschrift 3,027,483; German Offenlegungsschrift 3,145,422; Eur. J. Med. Chem. 1978, 13 (No. 2), pages 171-175; J. Heterocyclic Chem. 13 (1976), pages 491-496).

The α-oxyacetamides also required as starting materials for the process according to the invention are generally defined by the formula (III). In this formula, $R^1$ and $R^2$ preferably represent those radicals which were mentioned as preferred in the description of the corresponding radicals of the compounds of the formula (I), and $R''$ preferably represents hydrogen or a formyl, acetyl or benzoyl radical.

The compounds of the formula (III) are known or can be prepared in a simple manner by processes known per se (cf., for example, patent documents EP-A-0,005,501, EP-A-0,014,409, EP-A-0,018,497 and EP-A-0,029,171, German Offenlegungsschrift 2,201,432, German Offenlegungsschrift 2,904,490 and German Offenlegungsschrift 3,038,598).

Suitable diluents for the process according to the invention are organic or inorganic solvents. Preference is given to hydrocarbons such as toluene or cyclohexane, halogenohydrocarbons such as methylene chloride, chloroform, dichloroethane or chlorobenzene, ketones such as acetone or methyl isobutyl ketone, ethers such as diethyl ether, diisopropyl ether or methyl t-butyl ether, alcohols such as methanol, ethanol or isopropanol, amides such as dimethylformamide or dimethylacetamide, sulphoxides such as dimethyl sulphoxide, water or aqueous salt solutions.

Salts preferably used here are chlorides or sulphates of alkali metals or alkaline earth metals, for example sodium chloride, potassium chloride or calcium chloride. Sodium chloride is particularly preferred.

The process according to the invention is carried out using an acid acceptor. Strongly basic alkali metal and alkaline earth metal compounds, for example oxides such as sodium, potassium, magnesium and calcium oxides, hydroxides such as sodium, potassium, magnesium and calcium hydroxides, and/or carbonates such as sodium, potassium, magnesium and calcium carbonates, are preferably used as these acid-binding agents.

The addition of 0.01 to 10% by weight (based on α-oxyacetamide of the formula (III) used) of a phase transfer catalyst may prove advantageous in some cases. Examples of such catalysts which may be mentioned are: tetrabutylammonium iodide, tetrabutylammonium bromide, tributylmethylphosphonium bromide, trimethyl-$C_{13}/C_{15}$-alkylammonium chloride, dibenzyldimethylammonium methylsulphate, dimethyl-$C_{12}/C_{14}$-alkylbenzylammonium chloride, tetrabutylammonium hydroxide, 18-crown-6, triethylbenzylammonium chloride, trimethylbenzylammonium chloride, tetraethylammonium bromide and tetraethylammonium chloride.

The reaction temperature can be varied within a relatively wide range. In general, as indicated above, it is between $-50°$ C. and $+150°$ C., preferably between $-20°$ C. and $+100°$ C.

The process according to the invention is generally carried out at normal pressure, but it can also be carried out under elevated or reduced pressure, for example at between 0.1 and 10 bar.

To carry out the process according to the invention, 0.1 to 10 mols, preferably 0.8 to 1.2 mols, of oxyacetamide of the formula (III) and 0.5 to 10 mols, preferably 0.5 to 5 mols, of base are generally used per mol of sulphonylated heteroaromatic of the formula (II). The order in which the reactants are added can be altered at will; it is also possible for all the components to be metered into the reaction vessel at the same time. The reaction can be carried out continuously or batchwise. Working-up is carried out in the customary manner.

As is known, the compounds of the formula (I) which can be prepared by the process according to the invention can be used as herbicides (cf., for example, patent documents EP-A-0,005,501, EP-A-0,018,497, EP-A-0,029,171 and EP-A-0,060,426).

Preparation Examples

EXAMPLE 1

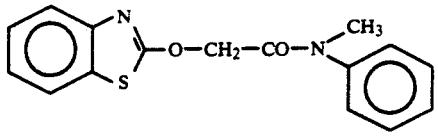

227 g (1 mol) of benzthiazol-2-yl ethyl sulphone and 165 g (1 mol) of N-methylhydroxyacetanilide are brought together in a 2-liter three-necked flask equipped with a stirrer, a thermometer and a dropping funnel, and the mixture is heated to 60° C. The clear melt is diluted with 200 g of saturated sodium chloride solution, with stirring. At an internal temperature of 50°-60° C., 400 g of sodium hydroxide solution (45%) are added dropwise and the reaction is then allowed to continue for a further two hours at 60° C. The mixture is then cooled to room temperature, diluted with 400 ml of water and filtered. The residue is washed on the suction filter with twice 200 ml of water and then dried at 70°-90° C. in vacuo.

This gives 283.0 g (95% of theory) of 2-(benzthiazol-2-yloxy)-N-methylacetanilide of melting point 130° C.

The starting material, benzthiazol-2-yl ethyl sulphone, is known (cf., for example, Chem. Abstr. Vol. 67, 89998k (1967); melting point 109°-110° C.).

EXAMPLE 2

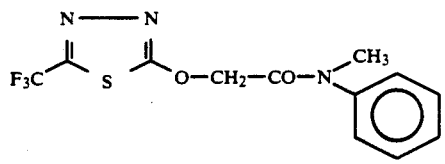

5.8 g (0.025 mol) of 2-methylsulphonyl-5-trifluoromethyl-1,3,4-thiadiazole, 4.4 g (0.026 mol) of N-methyl-2-hydroxyacetanilide, 3.8 g (0.038 mol) of potassium carbonate, 0.5 g of tetraethylammonium bromide and 50 ml of acetone are mixed in a 100 ml three-necked flask equipped with a stirrer and a thermometer, and the mixture is stirred for 20 hours at 20°-25° C. The undissolved salts are then filtered off and washed with acetone and the whole of the filtrate is freed of solvent in vacuo. The residue is taken up in 100 ml of diethyl ether, washed with dilute hydrochloric acid, dried over sodium sulphate and filtered, and the filtrate is freed of solvent in vacuo. The remaining oil crystallizes completely after a short time. 7.2 g (90.8% of theory) of 2-(5-trifluoromethyl-1,3,4-thiadiazol-2-yloxy)-N-methylacetanilide of melting point 63° C. are obtained.

Preparation of the Starting Material for Example 2

(a) 2-Methylthio-5-trifluoromethyl-1,3,4-thiadiazole

Firstly 210.7 g (1.53 mols) of phosphorus trichloride, and then 114 g (1 mol) of trifluoroacetic acid in 90 ml of toluene, are added dropwise, at $-5°$ to 0° C., to a mixture of 128 g (1 mol) of methyl dithiocarbazinate (96% pure), 260 ml of toluene and 87.1 g (1.1 mols) of pyridine. The reaction mixture is stirred overnight at room temperature, 100 ml of concentrated sulphuric acid are then added dropwise to the mixture at room temperature with slight cooling, and the resulting mixture is then heated at 45°-55° C. for 2 hours. After cooling, this is poured into a mixture of ice and toluene, the organic phase is separated off and the aqueous phase is re-extracted with toluene. The toluene phase is concentrated in vacuo; 169.9 g of 2-methylthio-5-trifluoromethyl-1,3,4-thiadiazole (≙ 82.4% of theory) remain in the form of a yellowish oil with a content of 97% (determined by gas chromatography); boiling point: 44° C./0.67 mbar.

(b)
2-Methylsulphonyl-5-trifluoromethyl-1,3,4-thiadiazole 0.2 g of sodium tungstate is added to a solution of 20 g (0.097 mol) of 2-methylthio-5-trifluoromethyl-1,3,4-thiadiazole (97% pure) in 70 ml of formic acid, and 27 g (0.26 mol) of 30% hydrogen peroxide are then added dropwise at room temperature; the temperature should not exceed 30° C. during this process. After the addition has ended, the reaction mixture is stirred for a further 2 hours at 30°-40° C., then taken up in methylene chloride and washed successively with an aqueous solution of sodium bisulphite and with water. The organic phase is dried and concentrated. This gives 19.1 g of 2-methylsulphonyl-5-trifluoromethyl-1,3,4-thiadiazole (≙ 85% of theory) in the form of white crystals of melting point 84° C. (Cf., in this context, patent documents DE-OS 1,817,069 and U.S. Pat. No. 3,562,284.)

The compounds given in the following Tables 1, 2a and 2b can also be prepared analogously:

TABLE 1

$$R-O-CH_2-CO-N\begin{matrix}R^1\\R^2\end{matrix} \qquad (I)$$

| Example No. | R | $R^1$ | $R^2$ | Physical data (M.p. °C./$n_D^{20}$) |
|---|---|---|---|---|
| 3 | 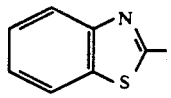 | $-C_2H_5$ | $-C_2H_5$ | 54 |
| 4 | 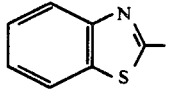 | $-CH_3$ | $-CH_3$ | 129 |
| 5 | 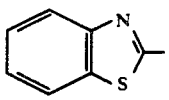 | $-CH_2-CH=CH_2$ | $-CH_2-CH=CH_2$ | 1.5781 |
| 6 | 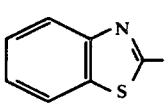 | \multicolumn{2}{c}{$-CH_2-CH_2-CH_2-CH_2-CH_2-CH-$ \newline $\phantom{xxxxxxxxxxxxxxxxxxxxx}CH_3$} | 81 |
| 7 | 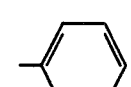 | $C_2H_5$ | 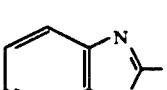 | 125 |
| 8 | 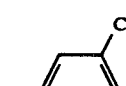 | $CH_3$ | 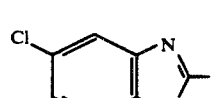 (with $CH_3$) | 118 |
| 9 | 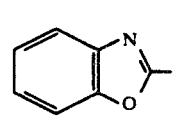 | \multicolumn{2}{c}{$-CH_2-CH_2-CH_2-CH_2-CH_2-CH_2-$} | 98 |
| 10 | 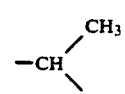 | $CH_3$ | $-CH\begin{matrix}CH_3\\C_2H_5\end{matrix}$ | 1.5983 |

TABLE 1-continued $$R-O-CH_2-CO-N\begin{matrix}R^1\\R^2\end{matrix}\qquad(I)$$

| Example No. | R | $R^1$ | $R^2$ | Physical data (M.p. °C./$n_D^{20}$) |
|---|---|---|---|---|
| 11 | 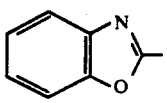 | $CH_3$ | $-CH\begin{matrix}CH_3\\|\\C\equiv CH\end{matrix}$ | 93 |
| 12 | 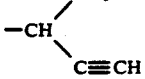 | $-CH_2-CH_2-OCH_3$ | $-CH_2-CH_2-OCH_3$ | Oil |
| 13 | 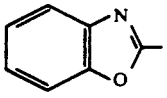 | $CH_3$ | 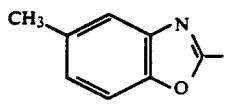 | 166 |
| 14 | 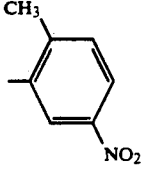 | $CH_3$ | 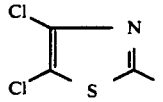 | 88 |
| 15 | 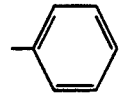 | $CH_3$ | $CH_3$ | 85 |
| 16 | 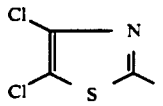 | $C_2H_5$ | $C_2H_5$ | 1.5394 |
| 17 | 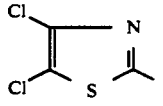 | $CH_3$ | 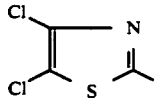 | 75 |
| 18 | 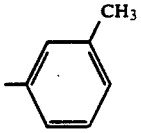 | $-CH_2-CH_2-CH_2-CH_2-CH-$<br>$\qquad\qquad\qquad\qquad\qquad\quad|$<br>$\qquad\qquad\qquad\qquad\qquad CH_3$ | | 1.5449 |
| 19 | 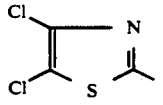 | $-CH_2-CH_2-CH-CH_2-CH_2-$<br>$\qquad\qquad\qquad|$<br>$\qquad\qquad\;CH_3$ | | 98 |
| 20 | 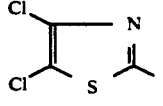 | $-CH_2-CH=CH_2$ | $-CH_2-CH=CH_2$ | 1.5418 |
| 21 | 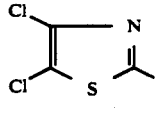 | $CH_3$ | $-CH-C\equiv CH$<br>$\;\;|$<br>$CH_3$ | Oil |
| 22 | 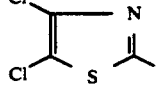 | $CH_3$ | $-CH\begin{matrix}CH_3\\C_2H_5\end{matrix}$ | 1.5357 |

TABLE 1-continued $$R-O-CH_2-CO-N\begin{matrix}R^1\\R^2\end{matrix}$$ (I)

| Example No. | R | $R^1$ | $R^2$ | Physical data (M.p. °C./$n_D^{20}$) |
|---|---|---|---|---|
| 23 | 3,4-dichloro-5-methyl-1,3-thiazol-2-yl (Cl, Cl on C=C; N, S in ring; =C(CH₃)- exocyclic) | \multicolumn{2}{c|}{—CH₂—CH₂—CH₂—CH₂—CH— with C₂H₅ branch} | 1.5440 |
| 24 | 5-methyl-3-(trifluoromethyl)-1,2,4-thiadiazol-... (F₃C, N—N, S ring) | CH₃ | C₆H₅ (phenyl) | Oil |
| 25 | 3-ethyl-5-methyl-1,2,4-thiadiazol-... (H₅C₂, N—N, S ring) | \multicolumn{2}{c|}{—C=C—CH₂—CH₂—CH₂— (fused phenyl)} | 1.5865 |
| 26 | 3-methyl-2-cyano-... (CH₃, NC, S, N, =C(CH₃)-) | CH₃ | 3-methylphenyl | 87–88 |
| 27 | 3-methyl-2-cyano-... (CH₃, NC, S, N, =C(CH₃)-) | CH₃ | C₆H₅ | 92–94 |
| 28 | Cl₃C-, N=, N—S ring, =C(CH₃)- | OCH₂ | —CH(CH₃)(C₂H₅) | 1.5230 |
| 29 | FCl₂C-, N=, N—S ring, =C(CH₃)- | CH₃ | C₆H₅ | 67 |
| 30 | i-C₃H₇-, N=, N—S ring, =C(CH₃)- | CH₃ | 4-chlorophenyl | 86 |
| 31 | n-C₃H₇-, N=, N—S ring, =C(CH₃)- | CH₃ | 4-chlorophenyl | 55 |
| 32 | CH₃S-, N=, N—S ring, =C(CH₃)- | CH₃ | C₆H₅ | 98 |
| 33 | CH₃S-, N=, N—S ring, =C(CH₃)- | \multicolumn{2}{c|}{—CH₂—CH₂—CH₂—CH₂—CH— with CH₃ branch} | 1.5560 |
| 34 | CH₃S-, N=, N—S ring, =C(CH₃)- | —CH₂—CH=CH₂ | —CH₂—CH=CH₂ | 1.5549 |

TABLE 1-continued $$R-O-CH_2-CO-N\begin{matrix}R^1\\R^2\end{matrix}\quad (I)$$

| Example No. | R | $R^1$ | $R^2$ | Physical data (M.p. °C./$n_D^{20}$) |
|---|---|---|---|---|
| 35 | i-C$_3$H$_7$-[4-isopropyl-1,2,5-thiadiazol-3-yl, 5-methyl] | \multicolumn{2}{c|}{—CH$_2$—CH$_2$—CH$_2$—CH$_2$—CH(C$_2$H$_5$)—} | 67 |
| 36 | i-C$_3$H$_7$-[4-isopropyl-1,2,5-thiadiazol-3-yl, 5-methyl] | \multicolumn{2}{c|}{—CH$_2$—CH$_2$—CH$_2$—CH$_2$—CH$_2$—CH$_2$—} | 60 |
| 37 | i-C$_3$H$_7$-[4-isopropyl-1,2,5-thiadiazol-3-yl, 5-methyl] | CH$_3$ | phenyl | 47 |
| 38 | C$_6$H$_5$—CH$_2$—S-[thiadiazolyl, 5-methyl] | \multicolumn{2}{c|}{—CH$_2$—CH$_2$—CH$_2$—CH$_2$—CH(CH$_3$)—} | 139 |
| 39 | Cl-[1,2,4-oxadiazol-3-yl, 5-methyl] | \multicolumn{2}{c|}{—CH$_2$—CH$_2$—CH$_2$—CH$_2$—CH(CH$_3$)—} | 53 |
| 40 | CH$_3$S-[1,2,4-oxadiazol-3-yl, 5-methyl] | CH$_3$ | 3-methyl-4-nitrophenyl | 192 |
| 41 | F$_3$C-[1,3,4-thiadiazol-2-yl, 5-methyl] | —CH$_2$—CH=CH$_2$ | —CH$_2$—CH=CH$_2$ | |
| 42 | F$_3$C-[1,3,4-thiadiazol-2-yl, 5-methyl] | —C$_3$H$_7$-n | —C$_3$H$_7$-n | |

TABLE 2a

[6-chlorobenzoxazol-2-yl]—O—CH$_2$—C(=O)—N(R$^1$)(R$^2$)

| Example No. | $R^1$ | $R^2$ or $-N\begin{matrix}R^1\\R^2\end{matrix}$ | | X | Melting Point |
|---|---|---|---|---|---|
| 43 | CH$_3$ | CH$_3$(CH$_2$)$_3$— | | O | 78–79° C. |
| 44 | | | 3-methylpiperidin-1-yl | O | 112° C. |

TABLE 2a-continued
| Example No. | R¹ | R² | or | -N(R¹)(R²) | X | Melting Point |
|---|---|---|---|---|---|---|
| 45 | | | |  | O | 82° C. |
| 46 | | | |  | O | 118° C. |
| 47 | $C_2H_5$ | $C_2H_5$ | | | O | 80° C. |
| 48 | $CH_3$ | $CH_3$ | | | O | |
| 49 | $CH_3(CH_2)_2-$ | $CH_3(CH_2)_2-$ | | | O | |
| 50 | $CH_3$ | |  | | O | |
| 51 | $CH_3$ | $CH_3$ | | | S | 160° C. |
| 52 | $C_2H_5$ | $C_2H_5$ | | | S | 76° C. |
| 53 | $CH_3$ | $CH_3(CH_2)_3-$ | | | S | 94° C. |
| 54 | $CH_3(CH_2)_2-$ | $CH_3(CH_2)_2-$ | | | S | 71° C. |
| 55 | $CH_3$ | |  | | S | |
| 56 | | | |  | S | 78° C. |
| 57 | | | |  | S | 98° C. |
| 58 | | | |  | S | 84° C. |
| 59 | $CH_2=CH-CH_2-$ | $CH_2=CH-CH_2-$ | | | S | 70° C. |
| 60 | | | |  | S | 88° C. |
| 61 | $CH_3O-$ | $\underset{C_2H_5-CH-}{\overset{CH_3}{|}}$ | | | S | |

TABLE 2a-continued
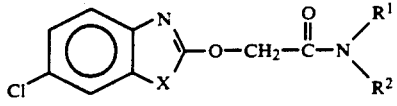
| Example No. | R¹ | R² or -N(R¹)(R²) | X | Melting Point |
|---|---|---|---|---|
| 62 | CH₃ | 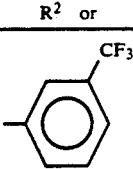 3-CF₃-phenyl | S | 144° C. |
| 63 | CH₃ | CH≡C—CH₂— | S | 115° C. |
| 64 | | 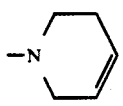 1,2,3,6-tetrahydropyridin-1-yl | S | 142° C. |
| 65 | | 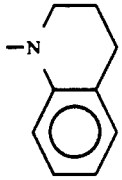 1,2,3,4-tetrahydroquinolin-1-yl | S | 162° C. |
| 66 | CH₃ | CH₃(CH₂)₂— | S | |
| 67 | CH₃ | CH₃OCH₂— | S | 77° C. |
| 68 | CH₃ | 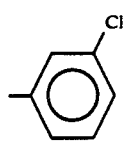 3-Cl-phenyl | S | 123° C. |
| 69 | CH₃ | 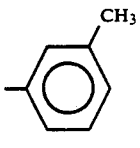 3-CH₃-phenyl | S | 126° C. |
| 70 | CH₃(CH₂)₃— | CH₃(CH₂)₃— | S | 67° C. |
| 71 | C₂H₅— | CH₂=CH— | S | 78° C. |
| 72 | CH₃ | 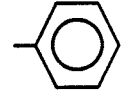 phenyl | S | 108° C. |
| 73 | CH₃ | 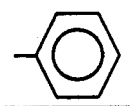 phenyl | O | 139° C. |

TABLE 2b

Structure: 6-chloro-benzoxazol-2-yl—O—CH₂—CO—N(R¹)(R²)

| Example No. | X | R¹ | R² or -N(R₁)(R₂) |
|---|---|---|---|
| 74 | O | CH₃ | CH₃O—CH₂— |
| 75 | O | CH₃ | cyclohexyl |
| 76 | O | CH₃ | cyclohex-3-enyl |
| 77 | O | CH₃ | F₃C—CH₂— |
| 78 | O | CH₃ | 2-methylphenyl |
| 79 | O | CH₃ | 3-methyl-4-nitrophenyl |
| 80 | O | CH₃ | 4-(trifluoromethyl)phenyl |
| 81 | O | C₂H₅ | CH₂=CH—CH₂— |
| 82 | O | CH₂=CH—CH₂— | CH₂=CH—CH₂— |
| 83 | O | | 3,5-dimethylpiperidin-1-yl |
| 84 | O | | 4-methylpiperidin-1-yl |
| 85 | O | | 1,2,3,4-tetrahydroquinolin-1-yl |

TABLE 2b-continued

[Structure: 6-chloro-benzoxazole/benzothiazole-2-yl-O-CH₂-CO-N(R¹)(R²)]

| Example No. | X | R¹ | R² or -N(R¹)(R²) |
|---|---|---|---|
| 86 | O | | piperidin-1-yl with 3-C₂H₅ substituent |
| 87 | O | CH₃ | HC≡C—CH₂— |
| 88 | O | CH₃O | C₂H₅—CH(CH₃)— |
| 89 | O | (CH₃)₂CHO— | C₂H₅O—CH₂CH₂—O— |
| 90 | O | CH₃ | 3-chlorophenyl |
| 100 | O | CH₃ | 3-(CF₃)phenyl |
| | S | CH₃ | CH₃O—CH₂— |
| | S | CH₃ | HC≡C—CH₂— |
| 101 | S | CH₃ | cyclohexyl |
| 102 | S | CH₃ | cyclohexenyl |
| 103 | S | CH₃ | F₃C—CH₂— |
| 104 | S | CH₃ | 3-(CF₃)phenyl |
| 105 | S | CH₃ | 3-chlorophenyl |
| 106 | S | CH₃ | 3-methylphenyl |

TABLE 2b-continued $$\text{Cl-benzo[X]azol-2-yl-O-CH}_2\text{-CO-N(R}^1\text{)(R}^2\text{)}$$

| No. | X | R¹ | R² |
|---|---|---|---|
| 107 | S | CH₃ | 4-methyl-3-nitrophenyl |
| 108 | S | CH₃— | 4-(F₃C)phenyl— |
| 109 | S | CH₃O— | C₂H₅—CH(CH₃)— |
| 110 | S | (CH₃)₂CHO— | (CH₃)₂CH— |
| 111 | S | C₂H₅ | CH₂=CH—CH₂— |
| 112 | S | \multicolumn{2}{|c|}{3,5-dimethylpiperidin-1-yl} |
| 113 | S | \multicolumn{2}{|c|}{3-ethylpiperidin-1-yl} |
| 114 | O | \multicolumn{2}{|c|}{piperidin-1-yl} |
| 115 | S | \multicolumn{2}{|c|}{2-ethylpiperidin-1-yl} |
| 116 | O | \multicolumn{2}{|c|}{2-ethylpiperidin-1-yl} |
| 117 | O | CH₃— | CH₂=CH—CH₂— |
| 118 | S | CH₃— | CH₂=CH—CH₂— |
| 119 | O | CH₃O—CH₂— | C₂H₅—CH(CH₃)— |
| 120 | S | CH₃O—CH₂— | C₂H₅—CH(CH₃)— |
| 121 | O | CH₃(CH₂)₃— | CH₃(CH₂)₃— |
| 122 | O | C₂H₅— | (CH₃)₂CH— |
| 123 | S | C₂H₅— | (CH₃)₂CH— |
| 124 | O | (CH₃)₂CH— | C₂H₅OCH₂CH₂—O— |

TABLE 2b-continued
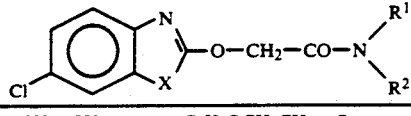
| | X | R¹ | R² |
|---|---|---|---|
| 125 | S | (CH₃)₂CH— | C₂H₅OCH₂CH₂—O— |
| 126 | O | CH₃— | 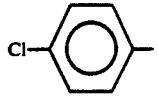 4-Cl-C₆H₄— |
| 127 | S | CH₃— | 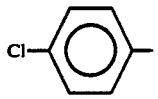 4-Cl-C₆H₄— |
| 128 | S | CH₃— | 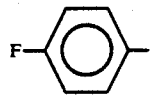 4-F-C₆H₄— |
| 129 | S | CH₃— | 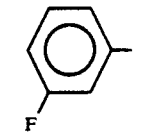 3-F-C₆H₄— |
| 130 | O | CH₃— | 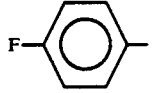 4-F-C₆H₄— |
| 131 | O | CH₃— | 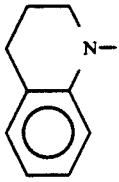 (1,2,3,4-tetrahydroquinolin-1-yl) |
| 132 | S | CH₃— | 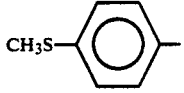 4-CH₃S-C₆H₄— |
| 133 | O | CH₃— | 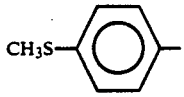 4-CH₃S-C₆H₄— |
| 134 | S | CH₃— | 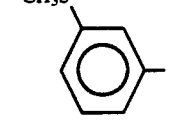 3-CH₃S-C₆H₄— |
| 135 | S | CH₃— | 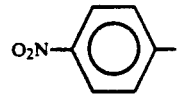 4-O₂N-C₆H₄— |
| 136 | O | CH₃— | 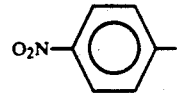 4-O₂N-C₆H₄— |
| 137 | O | CH₃— | n-H₉C₄— |
| 138 | S | CH₃— | n-H₉C₄— |

TABLE 2b-continued

| | | |
|---|---|---|
| 139 | O | piperidine-type ring (tetrahydropyridine) |
| 140 | S | piperidine-type ring (tetrahydropyridine) |
| 141 | O | dihydropyridine-type ring |

It will be understood that the specification and examples are illustrative but not limitative of the present invention and that other embodiments within the spirit and scope of the invention will suggest themselves to those skilled in the art.

What is claimed is:

1. A process for the preparation of a heteroaryloxyacetamide of the formula $$R-O-CH_2-CO-N\begin{subarray}{l}R^1\\R^2\end{subarray}$$

in which
R is a 5-membered heterocycle containing as heteroatoms 1 to 3 nitrogen atoms and in addition an oxygen atom or a sulphur atom, which may be benzo-fused and which is optionally substituted by halogen, cyano, nitro, alkyl, alkoxy or alkylthio each having up to 4 carbon atoms, halogenoalkyl having up to 4 carbon atoms and up to 9 halogen atoms, aralkyl, aralkoxy or aralkylthio each having 6 or 10 carbon atoms in the aryl moiety and 1 to 2 carbon atoms in the alkyl moiety, and/or aryl having 6 or 10 carbon atoms which is optionally substituted up to three times by $C_{1-4}$-alkyl, $C_{1-4}$-alkoxy, halogen and/or $C_{1-4}$-halogenoalkyl, and $R^1$ and $R^2$ each independently is hydrogen, alkyl having 1 to 8 carbon atoms, alkenyl or alkynyl each having 2 to 8 carbon atoms, cycloalkyl or cycloalkenyl each having 3 to 7 carbon atoms and optionally substituted alkyl having 1 to 4 carbon atoms, alkoxy or alkoxyalkyl having 1 to 8 carbon atoms, halogenoalkyl having 1 to 8 carbon atoms and 1 to 5 halogen atoms, aralkyl having 6 to 10 carbon atoms in the aryl moiety and 1 to 2 carbon atoms in the alkyl moiety, and/or aryl having 6 or 10 carbon atoms which is optionally substituted by halogen, alkyl, alkoxy or alkylthio each having 1 to 4 carbon atoms, halogenoalkyl, halogenoalkoxy or halogenoalkylthio each having 1 to 2 carbon atoms and 1 to 5 halogen atoms, and/or nitro, or $R^1$ and $R^2$, together with the nitrogen atom to which they are bonded, form a 5-membered to 7-membered heterocycle which can contain up to 2 further nitrogen and/or oxygen atoms, alkyl having 1 to 6 carbon atoms, aryl having 6 or 10 carbon atoms, and/or dioxyalkylene having 2 to 3 carbon atoms, which comprises reacting a sulphonylated heteroaromatic of the formula $$R-SO_2-R'$$

in which
R' is lower alkyl or benzyl, with an α-oxyacetamide of the formula $$R''-O-CH_2-CO-N\begin{subarray}{l}R^1\\R^2\end{subarray}$$

in which
R" is hydrogen or acyl,
in the presence of an inorganic base as an acid acceptor and of solvent as a diluent at a temperature of about $-20°$ C. to $+100°$ C.

2. The process according to claim 1, wherein the reaction is effected in the presence of a phase transfer catalyst.

3. A process according to claim 1, in which
R is

[heterocyclic structures shown]

each of which can optionally be substituted by fluorine, chlorine, bromine, cyano, nitro, methyl, ethyl, n- or i-propyl, n-, i-, s- or t-butyl, methoxy, ethoxy, methylthio, tri-fluoromethyl, trichloromethyl, fluorodichloromethyl, difluorochloromethyl, benzyl, benzyloxy or benzylthio, as well as phenyl optionally substituted up to three times by methyl, methoxy, chlorine and/or trifluoromethyl, X is oxygen or sulphur, and R¹ and R² each independently is hydrogen, alkyl having 1 to 6 carbon atoms, alkenyl or alkynyl each having 2 to 8 carbon atoms, cycloalkyl or cycloalkenyl having 5 to 7 carbon atoms and optionally substituted up to three times by methyl or ethyl, alkoxy or alkoxyalkyl having 1 to 6 carbon atoms, halogenoalkyl having 1 to 6 carbon atoms and 1 to 5 halogen atoms, benzyl, or phenyl optionally substituted by up to three times by methyl, ethyl, methoxy, methylthio, trifluoromethyl, trifluoromethoxy, trifluoromethylthio, fluorine, chlorine and/or nitro, or R¹ and R², together with the nitrogen atom to which they are bonded, form a heterocycle of the formula

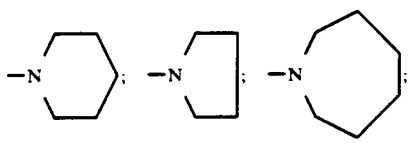

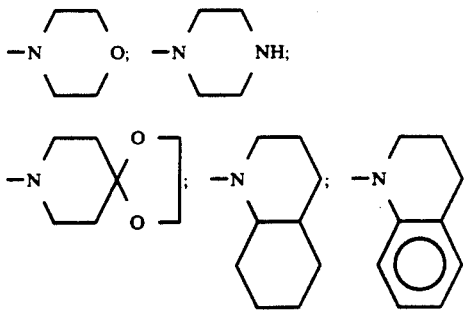

optionally substituted up to three times by methyl, ethyl and/or phenyl.

4. The process according to claim 3, wherein the reaction is carried out at a temperature of about −20° to +60° C.

5. The process according to claim 1, wherein benzthiazol-2-yl methyl sulphone or benzthiazol-2-yl ethyl sulphone is reacted with N-methylhydroxyacetanilide.

6. The process according to claim 1, wherein 2-methylsulphonyl-5-trifluoromethyl-1,3,4-thiadiazole or 2-ethylsulphonyl-5-trifluoromethyl-1,3,4-thiadiazole is reacted with N-methylhydroxyacetanilide.

* * * * *